US009788716B2

(12) United States Patent
Li

(10) Patent No.: US 9,788,716 B2
(45) Date of Patent: Oct. 17, 2017

(54) METHOD AND DEVICE OF TESTING COLOR BLINDNESS

(71) Applicant: BOE Technology Group Co., Ltd., Beijing (CN)

(72) Inventor: Hui Li, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 0 days.

(21) Appl. No.: 15/104,743

(22) PCT Filed: Sep. 15, 2015

(86) PCT No.: PCT/CN2015/089606
§ 371 (c)(1),
(2) Date: Jun. 15, 2016

(87) PCT Pub. No.: WO2016/176944
PCT Pub. Date: Nov. 10, 2016

(65) Prior Publication Data
US 2017/0119246 A1    May 4, 2017

(30) Foreign Application Priority Data
May 7, 2015 (CN) .......................... 2015 1 0229329

(51) Int. Cl.
*A61B 3/02* (2006.01)
*A61B 3/06* (2006.01)
(Continued)

(52) U.S. Cl.
CPC ............ *A61B 3/066* (2013.01); *A61B 3/0025* (2013.01); *A61B 3/113* (2013.01); *A61B 5/048* (2013.01); *A61B 5/04842* (2013.01)

(58) Field of Classification Search
CPC ......... A61B 3/066; A61B 3/032; A61B 3/024; A61B 3/06; A61B 3/0041
(Continued)

(56) References Cited

U.S. PATENT DOCUMENTS 2,462,485 A  2/1949 Freeman
6,220,708 B1  4/2001 Koest
(Continued)

FOREIGN PATENT DOCUMENTS

CN  103530624 A  1/2014
CN  104825128 A  8/2015
(Continued)

OTHER PUBLICATIONS

International Search Report and Written Opinion for International Application No. PCT/CN2015/089606, dated Jan. 8, 2016, 14 pages.
(Continued)

*Primary Examiner* — James Greece
(74) *Attorney, Agent, or Firm* — Westman, Champlin & Koehler, P.A.

(57) ABSTRACT

Embodiments of the present invention disclose a method and a device of testing color blindness, which belong to the technical field of test. The method includes: acquiring a plurality of preset coloring schemes, each of which is provided to test one type of color blindness and comprises a base color and a changing color; acquiring color sense test patterns, each of which corresponding to one of the coloring schemes; changing a color of at least a part of the grids in one of color sense test patterns one by one from the base color to the changing color according to the grid color-changing sequence of the corresponding color sense test pattern during displaying the corresponding color sense test pattern, when the corresponding color sense test pattern is
(Continued)

used to perform color blindness test on a tested person, and acquiring positions of the eyeballs of the tested person as the color of the grids is changing; obtaining a first fitting degree by fitting an acquired movement trace of the color point to a movement trace of the eyeballs; and, judging which type of color blindness of the tested person is according to the first fitting degree. According to the present invention, dependence analysis is performed on the movement trace of the eyeballs of the tested person and the movement trace of a color point in the corresponding color sense test pattern to obtain in quantitative sense which type of the color blindness of the tested person is, thereby increasing accuracy of the color blindness testing.

12 Claims, 8 Drawing Sheets

(51) Int. Cl.
*A61B 3/113* (2006.01)
*A61B 3/00* (2006.01)
*A61B 5/0484* (2006.01)
*A61B 5/048* (2006.01)

(58) Field of Classification Search
USPC .......................................... 351/242–243, 246
See application file for complete search history.

(56) References Cited

U.S. PATENT DOCUMENTS

| | | | |
|---|---|---|---|
| 2005/0105051 A1 | 5/2005 | Jones et al. | |
| 2013/0335435 A1* | 12/2013 | Ambrus | ................ G06T 19/20 |
| | | | 345/589 |
| 2015/0085258 A1 | 3/2015 | Ichikawa et al. | |

FOREIGN PATENT DOCUMENTS

| | | |
|---|---|---|
| EP | 2 839 771 A1 | 2/2015 |
| JP | H02-13426 A | 1/1990 |
| JP | 2012-35067 A | 2/2012 |

OTHER PUBLICATIONS

English translation of Box No. V of the Written Opinion for the International Searching Authority for International Application No. PCT/CN2015/089606, dated Jan. 8, 2016, 2 pages.
First Office Action, including Search Report, for Chinese Patent Application No. 201510229329.X, dated Dec. 28, 2015, 10 pages.

* cited by examiner

METHOD AND DEVICE OF TESTING COLOR BLINDNESS

CROSS-REFERENCE TO RELATED APPLICATIONS

This application is a Section 371 National Stage of International Application No. PCT/CN2015/089606, filed on 15 Sep. 2015, which has not yet published, which claims priority to Chinese Patent Application No. 201510229329.X, filed May 7, 2015, entitled "method and device of testing color blindness", which are incorporated herein by reference in their entirety.

BACKGROUND

Technical Field

The present invention relates to technical field of test, and particularly to a method and a device of testing color blindness.

Description of the Related Art

Color blindness is a congenital dyschromatopsia. A person with color blindness cannot discriminate various colors or a certain color in nature spectrum. A person with color weakness has a weak color discrimination ability, that is, exhibits weak or poor ability of color discrimination though he may see colors that a normal person can see, and can hardly discriminate color like a color-blindness person under dull condition or exhibits color sense fatigue. In practice, particularly in fields of transportation, medical science, textile industry, instrument, and art, absence of common color discrimination ability will render serious inconvenience. Thus, color-blindness test is a common physical test in our country.

Currently, there are mainly four approaches to test a color blindness, including color sense test table, color discrimination testing device, strip show test and color blindness testing inspectoscope. During a color blindness test using the above approaches, the tested person is easily subject to disturb from a medical and exterior physical environment so that a result of this test cannot reveal degree of color blindness of the tested person in quantitative sense. Further, the existing approaches have poor versatility and rationality due to their different testing standards and concepts. In addition, some person with color weakness might memorize keys to the testing table for color sense in order to muddle through in the physical examination and obtain qualification such as professional entrance qualification, or driving license, etc., causing adverse consequences.

SUMMARY OF THE INVENTION

In order to solve the problem in the prior arts, embodiments of present invention provide a method and a device of testing color blindness. The schemes may be as below.

In an aspect, there is provided a method of testing color blindness, the method comprising:

acquiring a plurality of preset coloring schemes, each of which is provided to test a type of color blindness and comprises a base color and a changing color;

acquiring color sense test patterns, each of which corresponding to one of the coloring schemes and including a plurality of grids, each of the plurality of grids storing position coordinates thereof, the base color, the changing color and a grid color-changing sequence;

changing a color of at least a part of the grids in one of the color sense test patterns one by one from the base color to the changing color according to the grid color-changing sequence of the corresponding color sense test pattern during displaying the corresponding color sense test pattern, when the corresponding color sense test pattern is used to perform color blindness test on a tested person, and acquiring positions of the eyeballs of the tested person as the color of the grids is changing;

acquiring a movement trace of a color point, the movement trace of the color point being determined by the color-changing grid;

acquiring a movement trace of the eyeballs based on the positions of the eyeballs of the tested person;

obtaining a first fitting degree by fitting the movement trace of the color point to the movement trace of the eyeballs; and judging which type of color blindness of the tested person is according to the first fitting degree.

Optionally, the step of judging which type of color blindness of the tested person is according to the first fitting degree comprises:

comparing the first fitting degree with a first preset numerical value;

determining that the tested person does not belong to the type of color blindness tested by the corresponding color sense test pattern when the first fitting degree is greater than or equal to the first preset numerical value; and determining that the tested person belongs to the type of color blindness tested by the corresponding color sense test pattern when the first fitting degree is smaller than the first preset numerical value.

Optionally, the method further comprises:

making each of the color-changed grids flash for a specify time period at preset frequency, during the color of the at least part of the grids in the corresponding color sense test pattern changing one by one from the base color to the changing color, and acquiring brain wave signals received by the tested person when the color-changed grid flashes;

performing a wave filtering process and a power spectrum analysis on the brain wave signals received by the tested person during the each of the color-changed grids flashing, and then considering a frequency value corresponding to a greatest power value in the power spectrum as a frequency value of the brain wave signals received by the tested person when the color-changed grid flashes;

acquiring a color point flash curve that is determined by the frequency value, at which the color-changed grid flashes;

acquiring a brain wave signal curve that is determined by the frequency value of the brain wave signals received by the tested person;

acquiring a second fitting degree by fitting the color point flash curve to the brain wave signal curve; and judging which type of color blindness of the tested person is according to the first fitting degree and the second fitting degree.

Optionally, the step of judging which type of color blindness of the tested person is according to the first fitting degree and the second fitting degree comprises:

determining that the tested person does not belong to the type of color blindness to be determined by the corresponding color sense test pattern when the first fitting degree is greater than or equal to the first preset numerical value and the second fitting degree is greater or equal to the second preset numerical value;

determining that the tested person belongs to the type of color blindness to be determined by the corresponding color sense test pattern when the first fitting degree is greater than or equal to the first preset numerical value but the second fitting degree is smaller than the second preset numerical value; and determining that the tested person belongs to the type of color blindness to be determined by the corresponding color sense test pattern when the first fitting degree is smaller than the first preset numerical value and the second fitting degree is smaller than the second preset numerical value.

Optionally, after the step of judging which type of color blindness of the tested person is according to the first fitting degree, the method further comprises:

acquiring testing results corresponding respectively to the color sense test patterns when the test on the tested person by using all the color sense test patterns is finished;

performing weighting operations on the testing results corresponding to all the color sense test patterns based on weight values preset respectively for the color sense test patterns, to acquire a result value of weighting operations; and determining degree of the color blindness of the tested person according to the result value of weighting operations.

Optionally, the step of determining degree of the color blindness of the tested person according to the results of weighting operations comprises:

determining that the tested person has no achromatopsia symptom when the result value is greater than or equal to a first number;

determining that the tested person has mild achromatopsia symptom when the result value is greater than or equal to a second number but smaller than the first number;

determining that the tested person has moderate achromatopsia symptom when the result value is greater than or equal to a third number but smaller than the second number; and determining that the tested person has severe achromatopsia symptom when the result value is greater than or equal to a fourth number but smaller than the third number;

wherein the first number is greater than the second number, the second number is greater than the third number and the third number is greater than the fourth number.

In another aspect, there is provided a color blindness testing device, comprising:

a first acquisition module configured to acquire a plurality of preset coloring schemes, wherein each of the coloring schemes is provided to test one type of color blindness and includes a base color and a changing color;

a second acquisition module configured to acquire color sense test patterns, wherein each of the color sense test patterns corresponds to one of the coloring schemes and includes a plurality of grids, each of the plurality of grids storing position coordinates thereof, the base color, the changing color and a grid color-changing sequence;

a color changing module configured to change a color of at least a part of the grids in one of the color sense test patterns one by one from the base color to the changing color according to the grid color-changing sequence of the corresponding color sense test pattern during displaying the corresponding color sense test pattern, when of the corresponding color sense test pattern is used to perform color blindness test on a tested person;

a third acquisition module configured to acquire positions of the eyeballs of the tested person as the color of the grids is changing;

a fourth acquisition module configured to acquire a movement trace of a color point, the movement trace of a color point being determined by the color-changing grid;

a fifth acquisition module configured to acquire a movement trace of the eyeballs based on the positions of the eyeballs of the tested person;

a first fitting module configured to obtain a first fitting degree by fitting the movement trace of the color point to the movement trace of the eyeballs; and a first judging module configured to judge which type of color blindness of the tested person is according to the first fitting degree.

Optionally, the first judging module is configured, to compare the first fitting degree with a first preset numerical value; to determine that the tested person does not belong to the type of color blindness tested by the corresponding color sense test pattern when the first fitting degree is greater than or equal to the first preset numerical value; and to determine the tested person belongs to the type of color blindness tested by the corresponding color sense test pattern when the first fitting degree is smaller than the first preset numerical value.

Optionally, the device further comprises:

a flashing module configured to make each of the color-changed grids flash for a specify time period at preset frequency, during the color of the at least part of the grids in the corresponding color sense test pattern changing one by one from the base color to the changing color;

a sixth acquisition module configured to acquire brain wave signals received by the tested person when the color-changed grid flashes;

a seventh acquisition module configured to perform a wave filtering process and a power spectrum analysis on the brain wave signals received by the tested person during the each of the color-changed grids flashing, and then consider a frequency value corresponding to a greatest power value in the power spectrum as a frequency value of the brain wave signals received by the tested person when the color-changed grid flashes;

an eighth acquisition module configured to acquire a color point flash curve that is determined by the frequency value, at which the color-changed grid flashes;

a ninth acquisition module configured to acquire a brain wave signal curve that is determined by the frequency value of the brain wave signals received by the tested person;

a second fitting module configured to acquire a second fitting degree by fitting the color point flash curve to the brain wave signal curve; and a second judging module configured to judge which type of the color blindness the tested person is according to the first fitting degree and the second fitting degree.

Optionally, the second judging module is configured to determine that the tested person does not belong to the type of color blindness to be determined by the corresponding color sense test pattern when the first fitting degree is greater than or equal to the first preset numerical value and the second fitting degree is greater or equal to the second preset numerical value; to deter wine that the tested person belongs to the type of color blindness to be determined by the corresponding color sense test pattern when the first fitting degree is greater than or equal to the first preset numerical value and the second fitting degree is smaller than the second preset numerical value; to determine that the tested person belongs to the type of color blindness to be determined by the corresponding color sense test pattern when the first fitting degree is greater than or equal to the first preset numerical value but the second fitting degree is smaller than the second preset numerical value; and to determine that the tested person belongs to the type of color blindness to be determined by the corresponding color sense test pattern when the first fitting degree is smaller than the first preset numerical value and the second fitting degree is smaller than the second preset numerical value.

Optionally, the device further comprising:

a tenth acquisition module configured to acquire testing results corresponding respectively to the color sense test patterns when the test on the tested person by using all the color sense test patterns is finished;

an operation module configured to perform weighting operations on the testing results corresponding to all the color sense test patterns based on weight values preset respectively for the color sense test patterns, to acquire a result value of weighting operations; and a determining module configured to determine degree of the color blindness of the tested person according to the result value of weighting operations.

Optionally, the determining module is configured to determine that the tested person has no achromatopsia symptom when the result value is greater than or equal to a first number; to determine that the tested person has mild achromatopsia symptom when the result value is greater than or equal to a second number but smaller than the first number; to determine that the tested person has moderate achromatopsia symptom when the result value is greater than or equal to a third number but smaller than the second number; and to determine that the tested person has severe achromatopsia symptom when the result value is greater than or equal to a fourth number but smaller than the third number;

wherein the first number is greater than the second number, the second number is greater than the third number and the third number is greater than the fourth number.

The embodiments of the present invention may bring the following advantages.

When any of the color sense test patterns is used to perform color blindness test on the tested person, a color of at least a part of the grids in the corresponding color sense test pattern is changed one by one from the base color to the changing color according to the grid color-changing sequence of the corresponding color sense test pattern. During this process, positions of the eyeballs of a tested person are acquired as the color of the grids is changing, so that a movement trace of a color point and a movement trace of the eyeballs are acquired; and then the movement trace of the color point is fitted to the movement trace of the eyeballs so as to obtain a first fitting degree, thereby judging which type of color blindness of the tested person is. According to the present invention, dependence analysis is performed on the movement trace of the eyeballs of the tested person and the movement trace of the color point in the corresponding color sense test pattern to obtain in quantitative sense which type of the color blindness of the tested person is, thereby increasing accuracy of the color blindness testing.

BRIEF DESCRIPTION OF THE DRAWINGS

In order to provide a more clear understanding of technique solutions of embodiments of the present invention, there is provided a brief introduction of the attached drawings used in the following description of the embodiments. Obviously, the drawings mentioned in the following description belong to some embodiments of the present invention. However, for those skilled in the art, other drawings may be achieved on the basis of these attached drawings without involving any inventive steps.

DETAILED DESCRIPTION OF EMBODIMENTS

Embodiments of the present invention will be further described in detailed with reference to accompanying drawings, in order to make the object, schemes and advantages of the present invention more clear.

Figure 1:
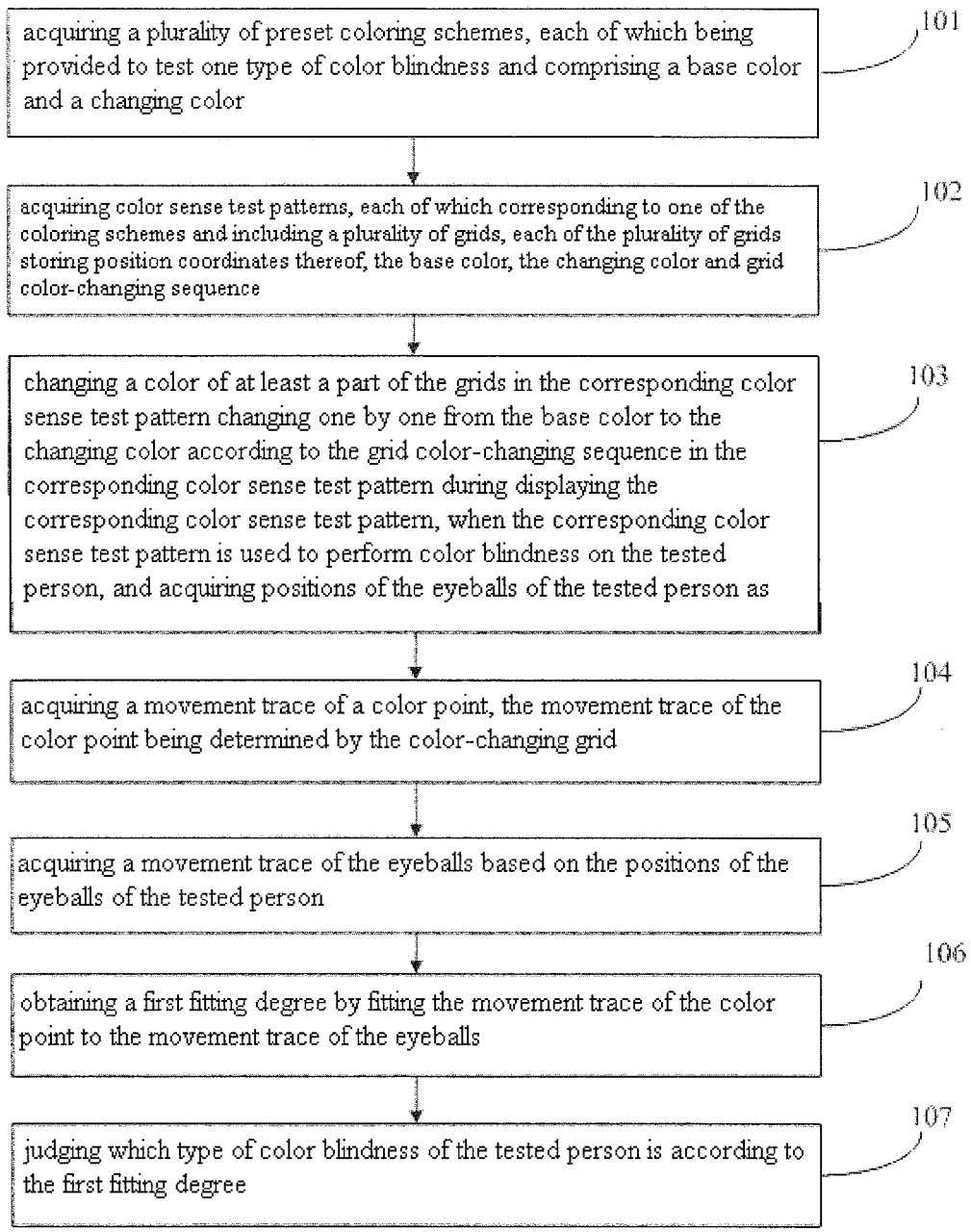
FIG. 1 is a flow chart of a method of testing color blindness according to an embodiment of the present invention.

Embodiments of the present invention provide a method of test color blindness. Referring to FIG. 1, a method according to the embodiments of the present invention includes the following steps.

Step 101, acquiring a plurality of preset coloring schemes, each of which is provided to test one type of color blindness and comprises a base color and a changing color.

Step 102, acquiring color sense test patterns, each of which corresponding to one of the coloring schemes and including a plurality of grids, each of the plurality of grids storing position coordinates thereof, the base color, the changing color and grid color-changing sequence.

Step 103, changing a color of at least a part of the grids in the corresponding color sense test pattern changing one by one from the base color to the changing color according to the grid color-changing sequence in the corresponding color sense test pattern during displaying the corresponding color sense test pattern, when the corresponding color sense test pattern is used to perform color blindness on the tested person, and acquiring positions of the eyeballs of the tested person as the color of the grids is changing.

Step 104, acquiring a movement trace of a color point, the movement trace of the color point being determined by the color-changing grid.

Step 105, acquiring a movement trace of the eyeballs based on the positions of the eyeballs of the tested person.

Step 106, obtaining a first fitting degree by fitting the movement trace of the color point to the movement trace of the eyeballs.

Step 107, judging which type of color blindness of the tested person is according to the first fitting degree.

According to the method provided by the embodiments of the present invention, when any of the color sense test patterns is used to perform color blindness on a tested person, a color of at least a part of the grids in the corresponding color sense test pattern is changed one by one from the base color to the changing color according to the grid color-changing sequence in the corresponding color sense test pattern. During this process, the positions of eyeballs of the tested person are acquired as the color of the grids is changing, so as to obtain a movement trace of a color point and a movement trace of the eyeballs, and then the movement trace of the color point is fitted to the movement trace of the eyeballs so as to obtain a first fitting degree, thereby judging which type of color blindness of the tested person is. According to the present invention, dependence analysis is performed on the movement trace of the eyeballs of the tested person and the movement trace of the color point in the corresponding color sense test pattern to obtain which type of the color blindness of the tested person in quantitative sense is, thereby increasing accuracy of the color blindness testing.

Optionally, the step of judging which type of color blindness of the tested person is according to the first fitting degree comprises:

comparing the first fitting degree with a first preset numerical value;

determining that the tested person does not belong to the type of color blindness tested by the corresponding color sense test pattern when the first fitting degree is greater than or equal to the first preset numerical value; and determining that the tested person belongs to the type of color blindness tested by the corresponding color sense test pattern when the first fitting degree is smaller than the first preset numerical value.

Optionally, the method further includes:

making each of the color-changed grids flash for a specify time period at preset frequency, during the color of the at least part of the grids in the corresponding color sense test pattern changing one by one from the base color to the changing color, and acquiring brain wave signals received by the tested person when the color-changed grid flashes;

performing a wave filtering process and a power spectrum analysis on the brain wave signals received by the tested person during the each of the color-changed grids flashing, and then considering a frequency value corresponding to a greatest power value in the power spectrum as a frequency value of the brain wave signals received by the tested person when the color-changed grid flashes;

acquiring a color point flash curve that is determined by the frequency value at which the color-changed grid flashes;

acquiring a brain wave signal curve that is determined by the frequency value of the brain wave signals received by the tested person;

acquiring a second fitting degree by fitting the color point flash curve to the brain wave signal curve; and judging which type of the color blindness the tested person is according to the first fitting degree and the second fitting degree.

Optionally, the step of judging which type of the color blindness the tested person is according to the first fitting degree and the second fitting degree comprises:

determining that the tested person does not belong to the type of color blindness to be determined by the corresponding color sense test pattern when the first fitting degree is greater than or equal to the first preset numerical value and the second fitting degree is greater or equal to the second preset numerical value;

determining that the tested person belongs to the type of color blindness to be determined by the corresponding color sense test pattern when the first fitting degree is greater than or equal to the first preset numerical value and the second fitting degree is smaller the second preset numerical value; and determining that the tested person belongs to the type of color blindness to be determined by the corresponding color sense test pattern when the first fitting degree is smaller than the first preset numerical value and the second fitting degree is smaller than the second preset numerical value.

Optionally, after judging which type of color blindness of the tested person is according to the first fitting degree, the method further comprises:

acquiring testing results corresponding respectively to the color sense test patterns when the test on the tested person by using all the color sense test patterns is finished;

performing weighting operations on the testing results corresponding to all the color sense test patterns based on weight values preset respectively for the color sense test patterns, to acquire a result value of weighting operations; and determining degree of the color blindness of the tested person according to the result value of weighting operations.

Optionally, the step of determining degree of the color blindness of the tested person according to the results of weighting operations comprises:

determining that the tested person has no achromatopsia symptom when the result value is greater than or equal to a first number;

determining that the tested person has mild achromatopsia symptom when the result value is greater than or equal to a second number and smaller than the first number;

determining that the tested person has moderate achromatopsia symptom when the result value is greater than or equal to a third number and smaller than the second number; and determining that the tested person has severe achromatopsia symptom when the result value is greater than or equal to a fourth number and smaller than the third number;

wherein the first number is greater than the second number, the second number is greater than the third number, and the third number is greater than the fourth number.

The above optional technical schemes may be combined in any manner to achieve optional embodiments of the present invention and are omitted here.

Figure 2:
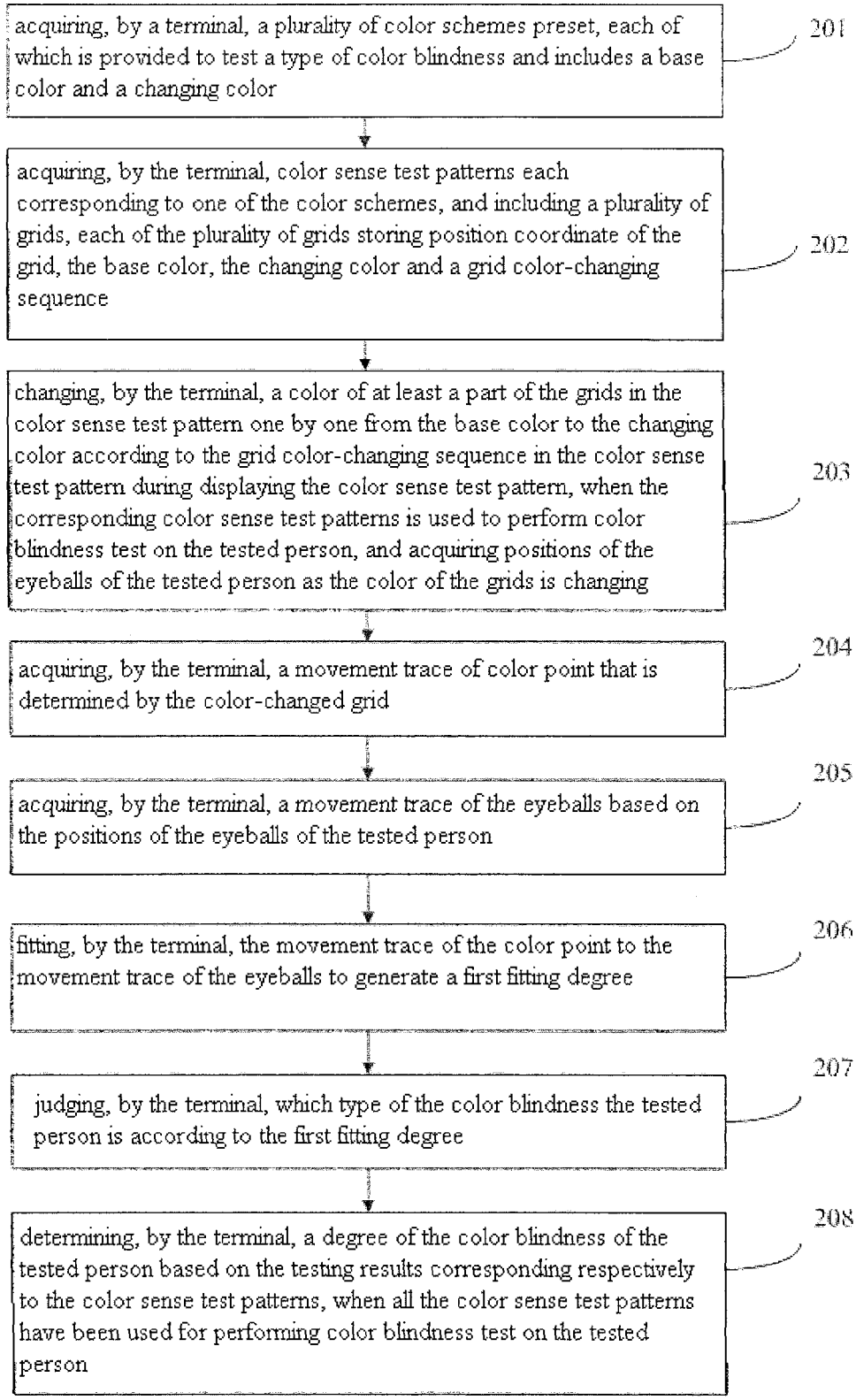
FIG. 2 is a flow chart of a method of testing color blindness according to another embodiment of the present invention.

Embodiments of the present invention provide a method of testing color blindness, which may be implemented in any types of terminals, such as a mobile phone, a television, a panel computer or other apparatus including display screen. The apparatus may be a liquid crystal display, an OLED display or a LED display, by which the color sense test patterns used for testing color blindness may be displayed. Referring to FIG. 2, the method according to an embodiment of the present invention includes:

a step 201 of: acquiring, by a terminal, a plurality of coloring schemes preset, each of which is provided to test a type of color blindness and includes a base color and a changing color.

Wherein, the color blindness may be classified as red color blindness, green color blindness, blue color blindness and total color blindness. It is known that a conventional method of testing color blindness is provided by considering that a person with different type of color blindness has different identification degree. That is, a person with red color blindness cannot discriminate red color from various colors, a person with green color blindness cannot discriminate green color from various colors, and a person with blue color blindness cannot discriminate blue color from various colors. However, in practice, a person with color blindness may encounter complex color discrimination situation. For example, the person with color blindness may discriminate red light in a crossing, but may not discriminate green light and yellow light. However, the person with color blindness cannot discriminate red and green in a color blindness test pattern composed of red, blue-green, yellow and purple, etc . . . . Thus, in order to improve accuracy of testing result of color blindness, it is necessary to provide different coloring schemes for testing different types of color blindness.

In the embodiment, the coloring schemes each may be used to test one type of color blindness and may include a base color and a changing color, in which the base color is an initial color of a grid in the color sense test pattern corresponding to the coloring scheme and the changing color is a color of the grid in the color sense test pattern whose color has been changed when testing the color blindness.

It is found by performing color blindness testing on lots of tested persons that, a tested person with green color blindness has a poorer discrimination ability on green and purple, a tested person with red color blindness has a poorer discrimination ability on red and blue-green and a tested person with blue color blindness has a poorer discrimination ability on yellow and blue. Due to different discrimination abilities of tested persons with different types of color blindness on different colors, various coloring schemes are preset in the embodiment. For example, a chromaticity coordinate with H, S and V is used to represent colors in a coloring scheme. When a tested person is tested whether he involves green color blindness, the colors in table 1.1 and table 1.2 may be used for test. Specifically, a row in table 1.1 may be selected randomly and then a color corresponding to the selected row in the chromaticity coordinate may be determined based on H, S, V coordinate that respectively correspond to the selected row. At the same time, a row in table 1.2 may be selected randomly and then a color corresponding to the selected row in the chromaticity coordinate may be determined based on H, S, V coordinate that respectively correspond to the selected row. Subsequently, one of the determined colors is used to be a base color and the other is a changing color.

TABLE 1.1

| sequence number | H | S | V |
|---|---|---|---|
| 1 | 179 | 141 | 163 |
| 2 | 169 | 127 | 163 |

TABLE 1.2

| sequence number | H | S | V |
|---|---|---|---|
| 1 | 332 | 82 | 193 |
| 2 | 309 | 68 | 183 |

When a tested person is tested whether he involves red color blindness, color in table 2.1 and table 2.2 may be used for the test. Specifically, a row in table 2.1 may be selected randomly and then color corresponding to the selected row in the chromaticity coordinate may be determined based on H, S, V coordinate that respectively correspond to the selected row. At the same time, a row in table 2.2 may be selected randomly and then color corresponding to the selected row in the chromaticity coordinate may be determined based on H, S, V coordinate that respectively correspond to the selected row. Subsequently, one of the determined colors is used to be a base color and the other is a changing color.

TABLE 2.1

| sequence number | H | S | V |
|---|---|---|---|
| 1 | 189 | 154 | 177 |
| 2 | 179 | 141 | 163 |

TABLE 2.2

| sequence number | H | S | V |
|---|---|---|---|
| 1 | 351 | 89 | 200 |
| 2 | 332 | 82 | 193 |

When a tested person is tested whether he involves blue color blindness, color in table 3.1 and table 3.2 may be used for testing. Specifically, a row in table 3.1 may be selected randomly and then color corresponding to the selected row in the chromaticity coordinate may be determined based on H, S, V coordinate that respectively correspond to the selected row. At the same time, a row in table 3.2 may be selected randomly and then color corresponding to the selected row in the chromaticity coordinate may be determined based on H, S, V coordinate that respectively correspond to the selected row. Subsequently, one of the determined colors is used to be a base color and the other is a changing color.

TABLE 3.1

| sequence number | H | S | V |
|---|---|---|---|
| 1 | 275 | 69 | 189 |

TABLE 3.2

| sequence number | H | S | V |
|---|---|---|---|
| 1 | 73 | 116 | 156 |
| 2 | 43 | 144 | 173 |

Step 202: acquiring, by the terminal, color sense test patterns each corresponding to one of the coloring schemes, and including a plurality of grids, each of the plurality of grids storing position coordinate of the grid, the base color, the changing color and a grid color-changing sequence.

Based on the coloring schemes determined in step 201, in step 202, the terminal may acquire the color sense test pattern corresponding to one of the coloring schemes by initiating the grids in the corresponding color sense test pattern, i.e., by adjusting all grids in the color sense test pattern to appear the base color, wherein the color sense test pattern is a test pattern for testing color blindness for the tested person and is composed of a plurality of circle grids adjoined to one another, and each of the plurality of grids stores position coordinate of the grid, the base color, the changing color and a grid color-changing sequence.

In the embodiment, position coordinate of each of the grids is needed to be determined before storing it. The approach of determining the position coordinate of each of the grids includes, but not limited to, providing a plane rectangular coordinate system based on a color sense test pattern and considering a coordinate where a center of each of the grids is as the position coordinate thereof; alternatively, equating a range in coordinate corresponding to a positional range in the rectangular coordinate system possessed by each of the grids to the position coordinate of the each of the grids. The approach is not limited in the embodiment. In addition, due to limitation of attention of the tested person, the tested person is hard to trace a plurality of grids which are changed in color when performing a color sense test on the tested person by using a color sense test pattern. Thus, the embodiment provides a method to preset a color-changing sequence for each of the grids according to a number/magnitude of color points composing of the color sense test pattern and a type of color blindness to be tested by the color sense test, so as to ensure only one grid is to be changed in color in a time period.

Step 203: changing, by the terminal, a color of at least a part of the grids in the color sense test pattern one by one from the base color to the changing color according to the grid color-changing sequence in the color sense test pattern during displaying the color sense test pattern, when the corresponding color sense test patterns is used to perform color blindness test on the tested person, and acquiring positions of the eyeballs of the tested person as the color of the grids is changing.

When performing the color blindness test on the tested person, for one color sense test pattern, the terminal may change the color of at least the part of the grids in the corresponding color sense test pattern one by one according to the color-changing sequence of each of the grids in the color sense test pattern during displaying the corresponding color sense test pattern. In this process, the terminal need recording a position coordinate of each of the grids and acquiring a position of eyeballs of the tested person when the color of the grid is changing.

The approach of acquiring the position of eyeballs of the tested person include, but not limited to, prompting a tested person to view a color sense test pattern by means of audio or characters when the corresponding color sense test pattern is used to perform color sense test on the tested person, and then recording a position of eyeballs of the tested person by activating a camera when a color of a grid in the corresponding color sense test pattern is changed.

It is noted that, as the color sense test pattern has a large number of grids, the color blindness test might waste time of the tested person if the color of each of the grids will be changed, and the tested person may become tired as viewing the color sense test pattern for a long period. Thus, it is enough to select an amount of grids of the color sense test pattern to perform the color sense test during changing the at least the part of the grids in the color sense test pattern one by one from the base color to the changing color according to the color-changing sequence of the grids in the color sense test pattern.

Figure 3:
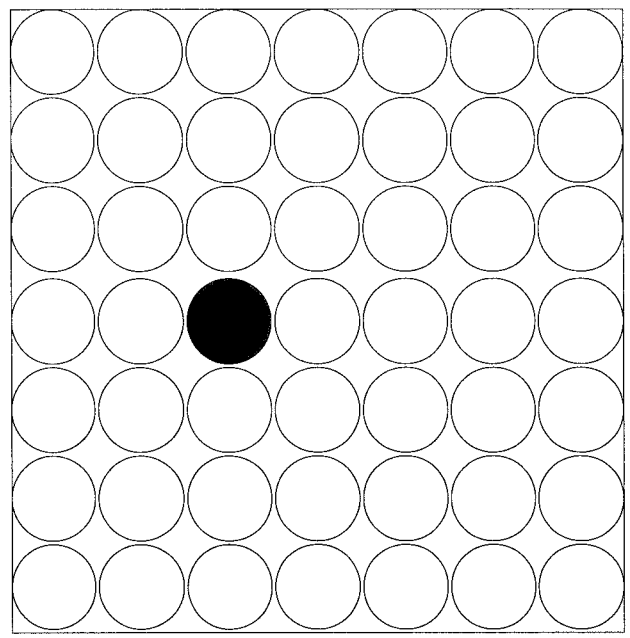
FIG. 3 is a trajectory chart of a color point changing trace according to another embodiment of the present invention.
Figure 3:
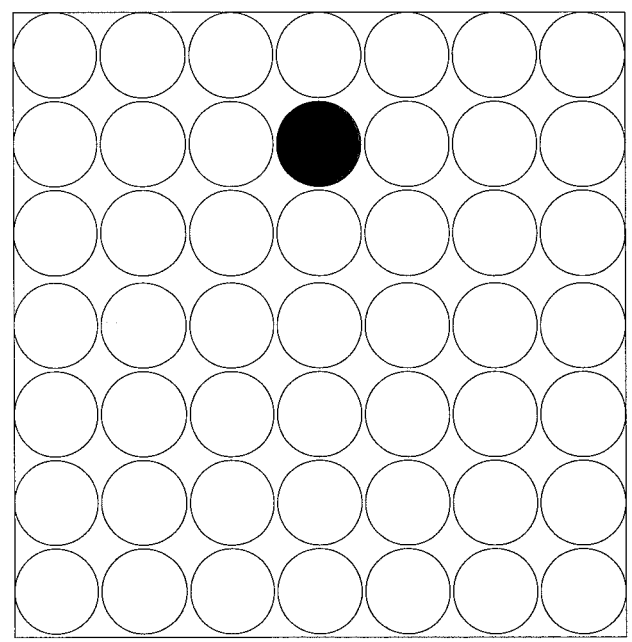
Figure 3:
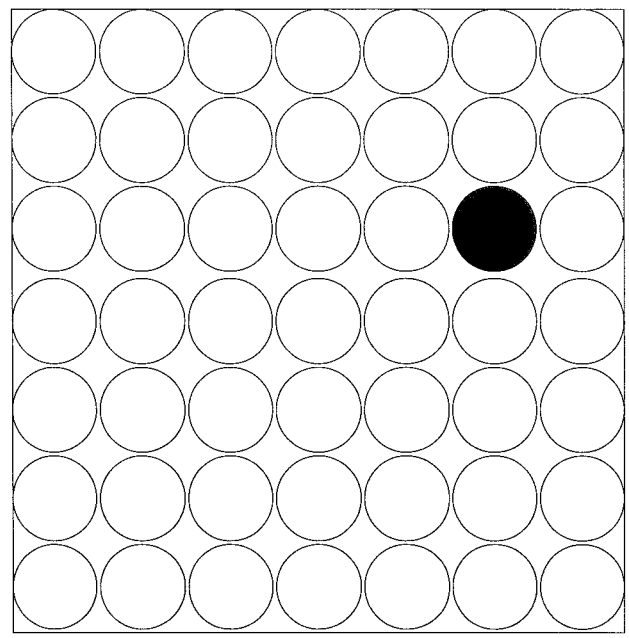
Figure 3:
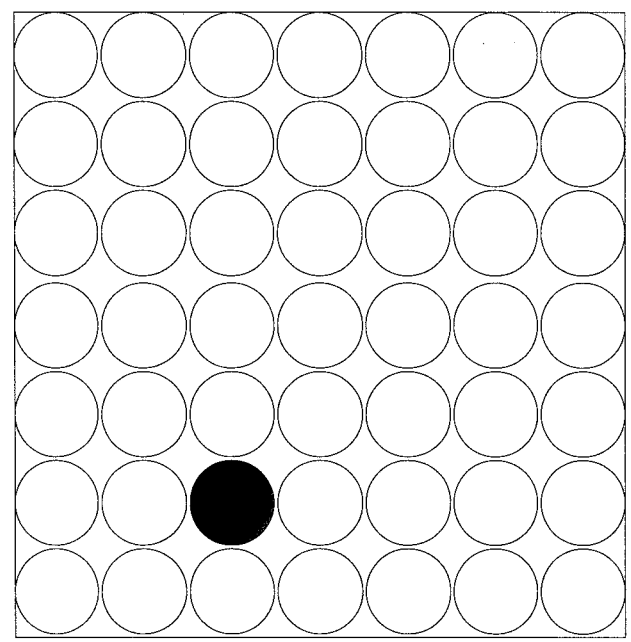
Figure 3:
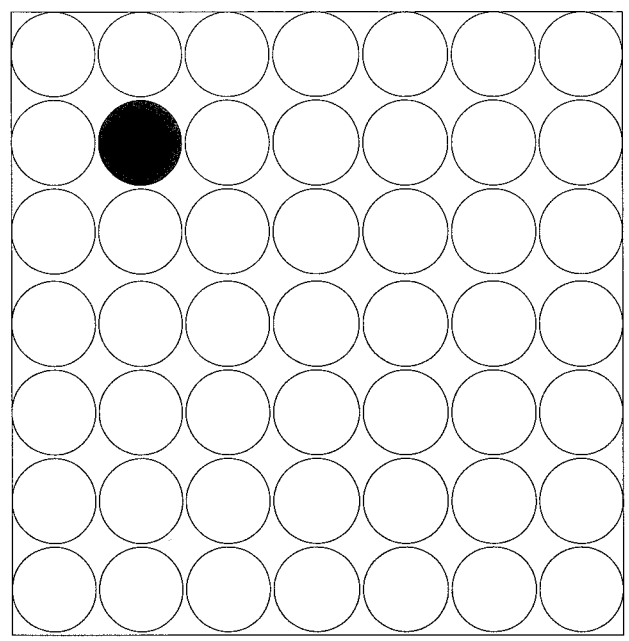

A specific embodiment is described in detail hereafter to understand the above process. Referring to FIG. 3, the color-changing sequence of the grids is presumed as shown in FIG. 3(a)~3(e). When performing a color blindness test on the tested person, the grid in line 4 and column 3, the grid in line 2 and column 4, the grid in line 3 and column 6, the grid in line 6 and column 3, and the grid in line 2 and column 2 in the color sense test pattern are changed in turn in color. In this process, the terminal will record a position coordinate of the color-changed grid, and activate the camera to record a position of eyeballs of the tested person.

Step 204: acquiring, by the terminal, a movement trace of color point that is determined by the color-changed grid.

Based on the position coordinate of the color-changed grid recorded in step 203, the terminal achieves a movement trace of the color point by labeling the acquired position coordinates of the color-changed grid in the coordinate system and joining the coordinates by a line according to the grid color-changing sequence.

Step 205: acquiring, by the terminal, a movement trace of the eyeballs based on the positions of the eyeballs of the tested person.

Based on the positions of the eyeballs recorded by the camera in step 203, the terminal achieves the movement trace of the eyeballs by labeling the acquired position coordinates of the eyeballs in the coordinate system and joining the coordinates by a line according to the grid color-changing sequence.

Step 206: fitting, by the terminal, the movement trace of the color point to the movement trace of the eyeballs to generate a first fitting degree.

Due to a high degree of approximation between the movement trace of the color point and the movement trace of the eyeballs, the type of color blindness of the tested person may be revealed in quantitative sense. For this reason, when performing color blindness test on the tested person, it is needed to fit the acquired movement trace of the color point to the movement trace of the eyeballs in the step.

Specifically, when the terminal fits the movement trace of the color point to the movement trace of the eyeballs, the movement trace of the color point and the movement trace of the eyeballs may be suitably zoomed so as to be represented in a same coordinate system. Then, the first fitting degree of the movement trace of the color point to the movement trace of the eyeballs may be determined according to amount of the color points in the movement trace of the color point that are overlapped with the movement trace of the eyeballs. For example, when performing a color blindness test, a color sense test pattern has ten color points, whose color are changed, and eight color points in a movement trace of the color point are overlapped with the movement trace of the eyeballs. In this instance, the first fitting degree is 8/10=80%.

Step 207: judging, by the terminal, which type of the color blindness the tested person is according to the first fitting degree.

The terminal may compare the first fitting degree with the first preset numerical value and then determine which type of the color blindness the test person is based on the comparison result, when judging which type of the color blindness the tested person is according to the first fitting degree. When the first fitting degree is greater than or equal to the first preset numerical value, the terminal determines that the tested person does not belong to the type of color blindness which is tested by the corresponding color sense test pattern; and, when the first fitting degree is smaller than the first preset numerical value, the terminal determines that the tested person belongs to the type of color blindness which is tested by the corresponding color sense test pattern. In this instance, the first preset numerical value may be 70%, 80%, etc . . . . However, the first preset numerical value is not limited to the embodiment.

It is noted that description is made by reference to testing a tested person by using one color sense test pattern, and other color sense test patterns may be used to test the tested person with respect to color blindness in similar way as that above. The description in detail is omitted.

In addition, in order to improve accuracy of color blindness testing for a person, the color blindness testing is performed several times on the tested person by using one color sense test pattern when performing the color blindness testing, so as to acquire an average of the testing results obtained by using repetitions of the one color sense test pattern and consider the average as the testing result of the color blindness testing for the tested person.

In order to overcome influence on the testing results from the factors, such as blink, movement, etc., which may render the testing results inaccurately, based on the above method of testing color blindness, the method according to the embodiment further includes modifying the testing results according to brain wave signals received from the tested person during the color blindness testing. The process includes the steps (1)~(6).

Step (1): making each of the color-changed grids flash for a specify time period at preset frequency, during the color of the at least part of the grids in the corresponding color sense test pattern changing one by one from the base color to the changing color, and acquiring brain wave signals received by the tested person when the color-changed grid flashes.

In the embodiment, the preset frequency may be 15 times per second, or 20 times per second, or etc . . . . It is not limited to the embodiment. The specify time period may be 2 second, 3 second, or 5 second, etc . . . . The specify time period is not limited to the embodiment either. During acquiring the brain wave signals received by the tested person when each of the color-changed grids flashes, a dry electrode may be used to record occipital lobe brain wave signals.

Step (2): performing a wave filtering process and a power spectrum analysis on the brain wave signals received by the tested person during the each of the color-changed grids flashing, and then considering a frequency value corresponding to a greatest power value in the power spectrum as a frequency value of the brain wave signals received by the tested person when the each of the color-changed grids flashes.

Step (3): acquiring a color point flash curve that is determined by the frequency value at which the color-changed grid flashes.

The flash frequency values of each of the grids is labeled in a frequency coordinate, in which the horizontal axis of the frequency coordinate represents the color-changed grid and the vertical axis thereof represents the flash frequency values corresponding respectively to the color-changed grids. Then, a color point flash curve may be obtained by joining the labeled points by a line according to the color-changing sequence of the grids.

Step (4): acquiring a brain wave signal curve that is determined by the frequency value of the brain wave signals received by the tested person.

The frequency values for the brain wave signals received by the brain of the tested person when each of the color-changed grids flashes are labeled in the frequency system, in which the horizontal axis of the frequency coordinate represents the color-changed grid and the vertical axis thereof represents the frequency values for the brain wave signals received by the tested person when each of the color-changed grids flashes. Then, the labeled points are joined by a line according to the color-changing sequence of the grids to generate a brain wave signal curve.

Step (5): acquiring a second fitting degree by fitting the color point flash curve to the brain wave signal curve.

The terminal may show the color point flash curve and the brain wave signal curve in the same coordinate system during fitting the color point flash curve to the brain wave signal curve, and determine the second fitting degree of the color point flash curve and the brain wave signal curve according to the number of the color points of the color point flash curve that are overlapped with the brain wave signal curve.

Step (6): judging which type of the color blindness the tested person is according to the first fitting degree and the second fitting degree.

The approaches of judging which type of the color blindness the tested person is according to the first fitting degree and the second fitting degree include, but not limited to, the followings:

determining that the tested person does not belong to the type of color blindness to be determined by the corresponding color sense test pattern when the first fitting degree is greater than or equal to the first preset numerical value and the second fitting degree is greater than or equal to the second preset numerical value; determining that the tested person belongs to the type of color blindness to be determined by the corresponding color sense test pattern when the first fitting degree is greater than or equal to the first preset numerical value but the second fitting degree is smaller than the second preset numerical value; and determining that the tested person belongs to the type of color blindness to be determined by the corresponding color sense test pattern when the first fitting degree is smaller than the first preset numerical value and the second fitting degree is smaller than the second preset numerical value.

In the embodiment, it is not necessary to define quantitative relations between the first present number and the second preset numerical value, that is, the first preset numerical value may be equal to the second preset numerical value, or the first preset numerical value may be not equal to the second preset numerical value. The embodiment is not limited to this.

Step 208: determining, by the terminal, a degree of the color blindness of the tested person based on the testing results corresponding respectively to the color sense test patterns, when all the color sense test patterns have been used for performing color blindness test on the tested person.

When all the color sense test patterns have been used for performing color blindness test on the tested person, the terminal is further configured to determine degree of the color blindness of the tested person based on the testing results corresponding respectively to the color sense test patterns. When color blindness test for the tested person is finished by using all the color sense test patterns, it is necessary for the terminal to acquire the testing results corresponding respectively to the color sense test patterns and perform weighting operations on the testing results corresponding respectively to all the color sense test patterns by means of weight values, each of which is provided for the corresponding color sense test pattern, so as to obtain a result of weighting operations, and finally determine degree of color blindness of the tested person according to the result of weighting operations.

The approaches of determinining degree of the color blindness of the tested person according to the result of weighting operations include, but not limited to, the following:

determinining that the tested person has no achromatopsia symptom when the result of the weighting operation is greater than or equal to the first number;

determining that the tested person has mild achromatopsia symptom when the result of the weighting operation is greater than or equal to a second number and smaller than the first number;

determining that the tested person has moderate achromatopsia symptom when the result value is greater than or equal to a third number and smaller than the second number; and determining that the tested person has severe achromatopsia symptom when the result value is greater than or equal to a fourth number and smaller than the third number;

wherein the first number is greater than the second number, the second number is greater than the third number, and the third number is greater than the fourth number. In the embodiment, the first number, the second number, the third number and the fourth number are not limited to any specify number.

Embodiments of the present invention provide a method in which, when any of the color sense test patterns is used to perform color blindness test on the tested person, a color of at least a part of the grids in the color sense test pattern is changed one by one from the base color to the changing color according to the grid color-changing sequence of the color sense test pattern. During this process, positions of the eyeballs of a tested person are acquired as the color of the grids is changing, so that a movement trace of a color point and a movement trace of the eyeballs are acquired; and then a first fitting degree is obtained by fitting the movement trace of the color point to the movement trace of the eyeballs, thereby judging which type of color blindness of the tested person is. According to the present invention, dependence analysis is performed on the movement trace of the eyeballs of the tested person and the movement trace of the color point in the color sense test pattern to obtain which type of the color blindness of the tested person in quantitative sense is, thereby increasing accuracy of the color blindness testing.

Figure 4:
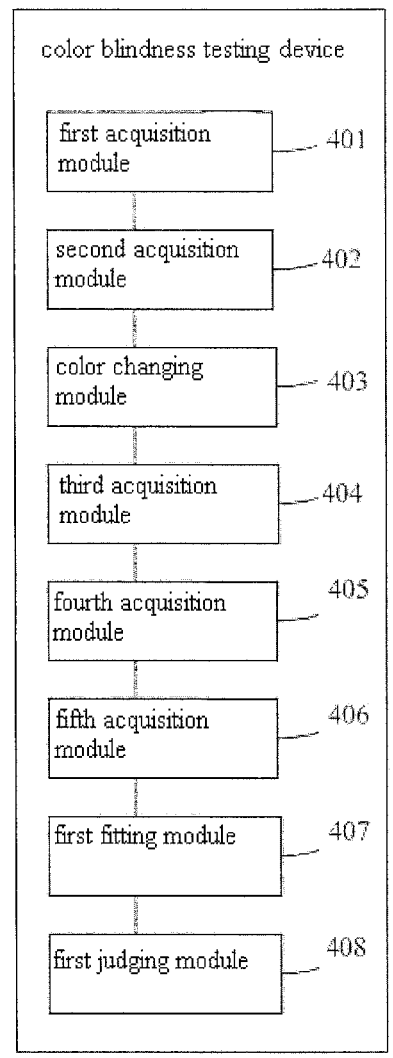
FIG. 4 is a structural schematic view of a color blindness testing device according to another embodiment of the present invention.

Referring to FIG. 4, an embodiment of the present invention provides a color blindness testing device, comprising:

a first acquisition module 401 configured to acquire a plurality of preset coloring schemes, wherein each of the coloring schemes is provided to test one type of color blindness and includes a base color and a changing color;

a second acquisition module 402 configured to acquire color sense test patterns, wherein each of the color sense test patterns corresponds to one of the coloring schemes and includes a plurality of grids, each of the plurality of grids storing position coordinates thereof, the base color, the changing color and a grid color-changing sequence;

a color changing module 403 configured to change a color of at least a part of the grids in one of the color sense test patterns one by one from the base color to the changing color according to the grid color-changing sequence in the color sense test pattern during displaying the color sense test pattern, when the corresponding color sense test pattern is used to perform color blindness test on a tested person;

a third acquisition module 404 configured to acquire positions of the eyeballs of the tested person as the color of the grids is changing;

a fourth acquisition module 405 configured to acquire a movement trace of a color point, the movement trace of a color point being determined by the color-changing grid;

a fifth acquisition module 406 configured to acquire a movement trace of the eyeballs based on the positions of the eyeballs of the tested person;

a first fitting module 407 configured to obtain a first fitting degree by fitting the movement trace of the color point to the movement trace of the eyeballs; and a first judging module 408 configured to judge which type of color blindness of the tested person is according to the first fitting degree.

In another embodiment of the present invention, the first judging module 408 is configured, to compare the first fitting degree with a first preset numerical value; to determine that the tested person does not belong to the type of color blindness tested by the color sense test pattern when the first fitting degree is greater than or equal to the first preset numerical value; and to determine the tested person belongs to the type of color blindness tested by the color sense test pattern when the first fitting degree is smaller than the first preset numerical value.

Figure 5:
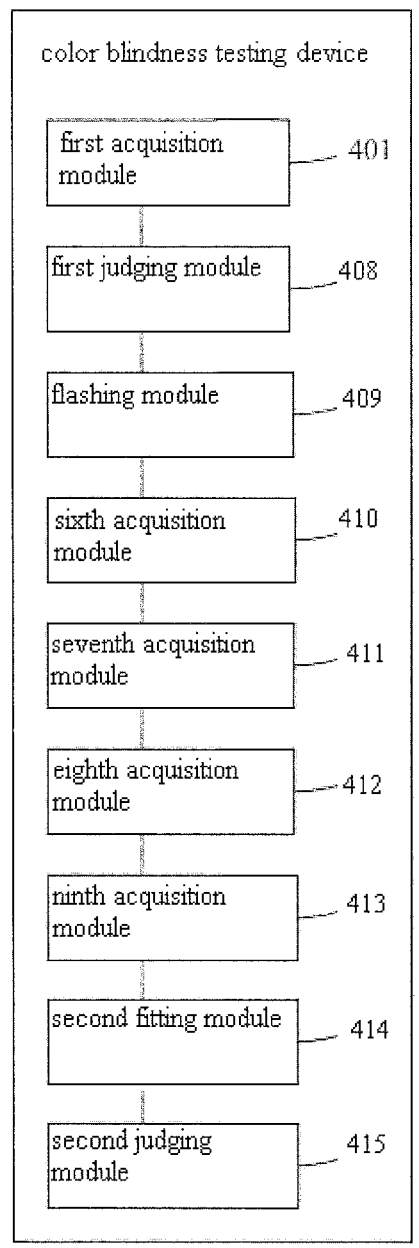
FIG. 5 is a structural schematic view of another color blindness testing device according to another embodiment of the present invention.

In another embodiment of the present invention, as shown in FIG. 5, in addition to the modules 401~408 included in the embodiment shown in FIG. 4, the device further includes:

a flashing module 409 is configured to make each of the color-changed grids flash for a specify time period at preset frequency, during the color of the at least part of the grids in the color sense test pattern changing one by one from the base color to the changing color;

a sixth acquisition module 410 configured to acquire brain wave signals received by the tested person when the color-changed grid flashes;

a seventh acquisition module 411 is configured to perform a wave filtering process and a power spectrum analysis on the brain wave signals received by the tested person during the each of the color-changed grids flashing, and then consider a frequency value corresponding to a greatest power value in the power spectrum as a frequency value of the brain wave signals received by the tested person when the color-changed grid flashes;

an eighth acquisition module 412 is configured to acquire a color point flash curve that is determined by the frequency value, at which the color-changed grid flashes;

a ninth acquisition module 413 is configured to acquire a brain wave signal curve that is determined by the frequency value of the brain wave signals received by the tested person;

a second fitting module 414 is configured to acquire a second fitting degree by fitting the color point flash curve to the brain wave signal curve; and a second judging module 415 is configured to judge which type of the color blindness the tested person is according to the first fitting degree and the second fitting degree.

The embodiment shown in FIG. 5 also include the modules 401~408 that are similar to the corresponding modules 401~408 in the embodiment in FIG. 4n and thus FIG. 5 shows the modules 401~408 in an omitted manner by omitting the modules 402~407.

In another embodiment of the present invention, the second judging module is configured, to determine that the tested person does not belong to the type of color blindness to be determined by the color sense test pattern when the first fitting degree is greater than or equal to the first preset numerical value and the second fitting degree is greater or equal to the second preset numerical value; to determine that the tested person belongs to the type of color blindness to be determined by the color sense test pattern when the first fitting degree is greater than or equal to the first preset numerical value but the second fitting degree is smaller than the second preset numerical value; and to determine that the tested person belongs to the type of color blindness to be determined by the color sense test pattern when the first fitting degree is smaller than the first preset numerical value and the second fitting degree is smaller than the second preset numerical value.

Figure 6:
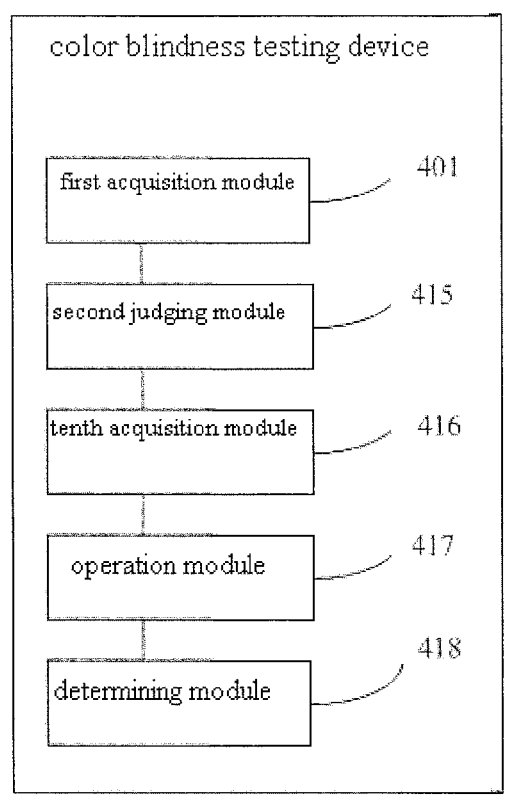
FIG. 6 is a structural schematic view of another color blindness testing device according to another embodiment of the present invention.

In another embodiment of the present invention, as shown in FIG. 6, in addition to the modules 401~415 included in the embodiment as shown in FIG. 5, the device further includes:

a tenth acquisition module 416 is configured to acquire testing results corresponding respectively to the color sense test patterns when the test on the tested person by using all the color sense test patterns is finished;

an operation module 417 is configured to perform weighting operations on the testing results corresponding to all the color sense test patterns based on weight values preset respectively for the color sense test patterns, to acquire a result value of weighting operations; and a determining module 418 is configured to determine degree of the color blindness of the tested person according to the result value of weighting operations.

The embodiment shown in FIG. 6 also include the modules 401-415 that are similar to the corresponding modules 401~415 in the embodiment in FIG. 5 and thus FIG. 6 shows the modules 401~415 in an omitted manner by omitting the modules 402~414.

In an another embodiment of the present invention, the determining module is configured, to determine that the tested person has no achromatopsia symptom when the result value is greater than or equal to a first number; to determine that the tested person has mild achromatopsia symptom when the result value is greater than or equal to a second number but smaller than the first number; to determine that the tested person has moderate achromatopsia symptom when the result value is greater than or equal to a third number but smaller than the second number; and to determine that the tested person has severe achromatopsia symptom when the result value is greater than or equal to a fourth number but smaller than the third number; wherein the first number is greater than the second number, the second number is greater than the third number and the third number is greater than the fourth number.

In sum, embodiments of the present invention provide a device by which, when any of the color sense test patterns is used to perform color blindness test on the tested person, a color of at least a part of the grids in the color sense test pattern is changed one by one from the base color to the changing color according to the grid color-changing sequence of the color sense test pattern. During this process, positions of the eyeballs of a tested person are acquired as the color of the grids is changing, so that a movement trace of a color point and a movement trace of the eyeballs are acquired; and then the movement trace of the color point is fitted to the movement trace of the eyeballs so as to obtain a first fitting degree, thereby judging which type of color blindness of the tested person is. According to the present invention, dependence analysis is performed on the movement trace of the eyeballs of the tested person and the movement trace of the color point in the color sense test pattern to obtain which type of the color blindness of the tested person in quantitative sense is, thereby increasing accuracy of the color blindness testing.

It is noted that the color blindness testing device according to the above embodiments is described as an example by means of various functional modules, and in use, its functions may be distributed to various functional modules as required, i.e., configuration of the color blindness testing device may be divided into different functional modules that may achieve all or part of the above functions. In addition, the color blindness testing device and the method of testing color blindness according to the above embodiments belong to the same concept and can be implemented as described in the embodiment of the method. The implementing process is omitted herein.

It is understood that those skilled in the art may implement all or part of the above embodiments by hardware or by introducing instructions by program to associated hardware, in which the program may be stored in a computer-readable memory medium. The mentioned memory medium may be read-only memory, magnetic disc or optical disc, etc . . . .

The above embodiments are only some preferred embodiments of the present invention, but not to limit the present invention. Any modification, equivalent, improvement, etc. made within the spirits and principle of the present invention, of the embodiments of the present invention should be included in the protective scope of the invention.

What is claimed is:

1. A method of testing color blindness, the method comprising:

acquiring a plurality of coloring schemes preset, each of which is provided to test one type of color blindness and comprises a base color and a changing color;

acquiring color sense test patterns, each of which corresponds to one of the coloring schemes and includes a plurality of grids, each of the plurality of grids storing position coordinates thereof, the base color, the changing color and a grid color-changing sequence;

changing a color of at least a part of the grids in one of the color sense test patterns one by one from the base color to the changing color according to the grid color-changing sequence of the corresponding color sense test pattern during displaying the corresponding color sense test pattern, when the corresponding color sense test pattern is used to perform color blindness test on a tested person, and acquiring positions of the eyeballs of the tested person as the color of the grids is changing;

acquiring a movement trace of a color point, the movement trace of the color point being determined by the color-changing grid;

acquiring a movement trace of the eyeballs based on the positions of the eyeballs of the tested person;

obtaining a first fitting degree by fitting the movement trace of the color point to the movement trace of the eyeballs; and judging which type of color blindness of the tested person is according to the first fitting degree.

2. The method according to claim 1, wherein the step of judging which type of color blindness of the tested person is according to the first fitting degree comprises:

comparing the first fitting degree with a first preset numerical value;

determining that the tested person does not belong to the type of color blindness tested by the corresponding color sense test pattern when the first fitting degree is greater than or equal to the first preset numerical value; and determining that the tested person belongs to the type of color blindness tested by the corresponding color sense test pattern when the first fitting degree is smaller than the first preset numerical value.

3. The method according to claim 1, wherein the method further comprises:

making each of the color-changed grids flash for a specify time period at preset frequency, during the color of the at least part of the grids in the corresponding color sense test pattern changing one by one from the base color to the changing color, and acquiring brain wave signals received by the tested person when the color-changed grid flashes;

performing a wave filtering process and a power spectrum analysis on the brain wave signals received by the tested person during the each of the color-changed grids flashing, and then considering a frequency value corresponding to a greatest power value in the power spectrum as a frequency value of the brain wave signals received by the tested person when the color-changed grid flashes;

acquiring a color point flash curve that is determined by the frequency value at which the color-changed grid flashes;

acquiring a brain wave signal curve that is determined by the frequency value of the brain wave signals received by the tested person;

acquiring a second fitting degree by fitting the color point flash curve to the brain wave signal curve; and judging which type of color blindness of the tested person is according to the first fitting degree and the second fitting degree.

4. The method according to claim 3, wherein the step of judging which type of color blindness of the tested person is according to the first fitting degree and the second fitting degree comprises:

determining that the tested person does not belong to the type of color blindness to be determined by the corresponding color sense test pattern when the first fitting degree is greater than or equal to the first preset numerical value and the second fitting degree is greater or equal to the second preset numerical value;

determining that the tested person belongs to the type of color blindness to be determined by the corresponding color sense test pattern when the first fitting degree is greater than or equal to the first preset numerical value and the second fitting degree is smaller than the second preset numerical value; and determining that the tested person belongs to the type of color blindness to be determined by the corresponding color sense test pattern when the first fitting degree is smaller than the first preset numerical value and the second fitting degree is smaller than the second preset numerical value.

5. The method according to claim 1, wherein after the step of judging which type of color blindness of the tested person is according to the first fitting degree, the method further comprises:

acquiring testing results corresponding respectively to the color sense test patterns when the test on the tested person by using all the color sense test patterns is finished;

performing weighting operations on the testing results corresponding to all the color sense test patterns based on weight values preset respectively for the color sense test patterns, to acquire a result value of weighting operations; and determining degree of the color blindness of the tested person according to the result value of weighting operations.

6. The method according to claim 5, wherein the step of determining degree of the color blindness of the tested person according to the results of weighting operations comprises:

determining that the tested person has no achromatopsia symptom when the result value is greater than or equal to a first number;

determining that the tested person has mild achromatopsia symptom when the result value is greater than or equal to a second number and smaller than the first number;

determining that the tested person has moderate achromatopsia symptom when the result value is greater than or equal to a third number and smaller than the second number; and determining that the tested person has severe achromatopsia symptom when the result value is greater than or equal to a fourth number and smaller than the third number;

wherein the first number is greater than the second number, the second number is greater than the third number, and the third number is greater than the fourth number.

7. A color blindness testing device, comprising:

a first acquisition module configured to acquire a plurality of coloring schemes preset, wherein each of the coloring schemes is provided to test one type of color blindness and includes a base color and a changing color;

a second acquisition module configured to acquire color sense test patterns, wherein each of the color sense test patterns corresponds to one of the coloring schemes and includes a plurality of grids, each of the plurality of grids storing position coordinates thereof, the base color, the changing color and a grid color-changing sequence;

a color changing module configured to change a color of at least a part of the grids in one of the color sense test patterns one by one from the base color to the changing color according to the grid color-changing sequence of the corresponding color sense test pattern during displaying the corresponding color sense test pattern, when the corresponding color sense test pattern is used to perform color blindness test on a tested person;

a third acquisition module configured to acquire positions of the eyeballs of the tested person as the color of the grids is changing;

a fourth acquisition module configured to acquire a movement trace of a color point, the movement trace of a color point being determined by the color-changing grid;

a fifth acquisition module configured to acquire a movement trace of the eyeballs based on the positions of the eyeballs of the tested person;

a first fitting module configured to obtain a first fitting degree by fitting the movement trace of the color point to the movement trace of the eyeballs; and a first judging module configured to judge which type of color blindness of the tested person is according to the first fitting degree.

8. The color blindness testing device according to claim 7, wherein the first judging module is configured, to compare the first fitting degree with a first preset numerical value; to determine that the tested person does not belong to the type of color blindness tested by the corresponding color sense test pattern when the first fitting degree is greater than or equal to the first preset numerical value; and to determine the tested person belongs to the type of color blindness tested by the corresponding color sense test pattern when the first fitting degree is smaller than the first preset numerical value.

9. The color blindness testing device according to claim 7, further comprising:

a flashing module configured to make each of the color-changed grids flash for a specify time period at preset frequency, during the color of the at least part of the grids in the corresponding color sense test pattern changing one by one from the base color to the changing color;

a sixth acquisition module configured to acquire brain wave signals received by the tested person when the color-changed grid flashes;

a seventh acquisition module configured to perform a wave filtering process and a power spectrum analysis on the brain wave signals received by the tested person during the each of the color-changed grids flashing, and then consider a frequency value corresponding to a greatest power value in the power spectrum as a frequency value of the brain wave signals received by the tested person when the color-changed grid flashes;

an eighth acquisition module configured to acquire a color point flash curve that is determined by the frequency value at which the color-changed grid flashes;
a ninth acquisition module configured to acquire a brain wave signal curve that is determined by the frequency value of the brain wave signals received by the tested person;
a second fitting module configured to acquire a second fitting degree by fitting the color point flash curve to the brain wave signal curve and
a second judging module configured to judge which type of the color blindness the tested person is according to the first fitting degree and the second fitting degree.

10. The color blindness testing device according to claim 9, wherein the second judging module is configured, to determine that the tested person does not belong to the type of color blindness to be determined by the corresponding color sense test pattern when the first fitting degree is greater than or equal to the first preset numerical value and the second fitting degree is greater or equal to the second preset numerical value; to determine that the tested person belongs to the type of color blindness to be determined by the corresponding color sense test pattern when the first fitting degree is greater than or equal to the first preset numerical value and the second fitting degree is smaller than the second preset numerical value; and to determine that the tested person belongs to the type of color blindness to be determined by the corresponding color sense test pattern when the first fitting degree is smaller than the first preset numerical value and the second fitting degree is smaller than the second preset numerical value.

11. The color blindness testing device according to claim 7, further comprising:
a tenth acquisition module configured to acquire testing results corresponding respectively to the color sense test patterns when the test on the tested person by using all the color sense test patterns is finished;
an operation module configured to perform weighting operations on the testing results corresponding to all the color sense test patterns based on weight values preset respectively for the color sense test patterns, to acquire a result value of weighting operations; and
a determining module configured to deter mine degree of the color blindness of the tested person according to the result value of weighting operations.

12. The color blindness testing device according to claim 11, wherein the determining module is configured, to determine that the tested person has no achromatopsia symptom when the result value is greater than or equal to a first number; to determine that the tested person has mild achromatopsia symptom when the result value is greater than or equal to a second number and smaller than the first number; to determine that the tested person has moderate achromatopsia symptom when the result value is greater than or equal to a third number and smaller than the second number; and to determine that the tested person has severe achromatopsia symptom when the result value is greater than or equal to a fourth number and smaller than the third number;
wherein the first number is greater than the second number, the second number is greater than the third number and the third number is greater than the fourth number.

* * * * *